United States Patent
Nir

(10) Patent No.: US 7,824,339 B2
(45) Date of Patent: Nov. 2, 2010

(54) METHOD AND SYSTEM FOR SELECTING AND RECORDING BIOPSY SITES IN A BODY ORGAN USING ULTRASOUND IN TWO AND THREE DIMENSIONS

(75) Inventor: Dror Nir, Brussels (BE)

(73) Assignee: Advanced Medical Diagnostics Holding S.A., Waterloo (BE)

( * ) Notice: Subject to any disclaimer, the term of this patent is extended or adjusted under 35 U.S.C. 154(b) by 972 days.

(21) Appl. No.: 11/251,435

(22) Filed: Oct. 14, 2005

(65) Prior Publication Data

US 2006/0079771 A1    Apr. 13, 2006

Related U.S. Application Data

(63) Continuation-in-part of application No. PCT/IB2004/001127, filed on Apr. 14, 2004, which is a continuation-in-part of application No. 10/413,591, filed on Apr. 15, 2003, now abandoned.

(51) Int. Cl.
*A61B 8/00* (2006.01)
(52) U.S. Cl. ...................................... 600/459; 382/128
(58) Field of Classification Search .................. 73/596; 600/437, 439, 443–447, 459; 382/128, 285–291
See application file for complete search history.

(56) References Cited

U.S. PATENT DOCUMENTS 6,351,660 B1    2/2002    Burke et al.
2005/0054924 A1*  3/2005  Dione et al. ................. 600/437

OTHER PUBLICATIONS

"Basic Principles of Ultrasound," downloaded on Feb. 17, 2010 from www.echo-web.com/html/echo-202-free/echo202-1-body.asp?code=, 6 pages.
Carson, et al. Pulse Echo Ultrasound Imaging Systems: Performance Tests and Criteria, General Medical Physics Committee Ultrasound Task Group, AAPM Report No. 8, pp. 1-73, Nov. 1980.
Stotzka, et al. "A New 3D Ultrasound Computer Tomography Demonstration System" Institute for Data Processing and Electronics, Forschungszentrum Karlsruhe, Germany, *Biomedizinische Technik*, pp. 176-177, 2004.

* cited by examiner

*Primary Examiner*—Brian Casler
*Assistant Examiner*—Parikha S Mehta
(74) *Attorney, Agent, or Firm*—Knobbe, Martens, Olson & Bear, LLP

(57) ABSTRACT

The present invention relates to methods and systems for selecting and recording biopsy sites in a body tissue or organ. More in particular the present invention provides a method for selecting and recording biopsy sites in a body organ comprising: a) obtaining a three-dimensional volume of backscattered Ultrasound data grid of a three-dimensional region of the organ; b) obtaining a two-dimensional matrix of Ultrasound data of a two-dimensional sub-region of said organ; c) positioning the two-dimensional matrix of Ultrasound data in the three-dimensional volume of backscattered Ultrasound data grid obtained in step (a); d) optionally selecting one or more sites in the two-dimensional matrix of Ultrasound data where a biopsy is to be obtained; e) indicating in the three-dimensional volume of backscattered Ultrasound data grid and/or in the two-dimensional matrix of Ultrasound data any sites at which biopsies were obtained; and f) optionally repeating steps (b) to (e) as required.

13 Claims, 3 Drawing Sheets

METHOD AND SYSTEM FOR SELECTING AND RECORDING BIOPSY SITES IN A BODY ORGAN USING ULTRASOUND IN TWO AND THREE DIMENSIONS

RELATED APPLICATIONS

This application is a continuation-in-part of PCT/IB2004/001127, filed Apr. 14, 2004, published in English, which is a continuation-in-part of U.S. application Ser. No. 10/413,591, filed Apr. 15, 2003, now abandoned.

FIELD OF THE INVENTION

The present invention relates to methods and systems for selecting and recording biopsy sites in a body tissue or organ.

BACKGROUND OF THE INVENTION

In the diagnosis of a clinical condition in a body tissue or organ, it is known to obtain a number of biopsies from the tissue or organ. For example, in the diagnosis of prostate or breast cancer, a region of the organ is imaged using ultrasonic radiation. The practitioner obtains a 2D image of the region of the organ and then, based on the image, selects a site in the organ from where a biopsy is to be obtained. A cannula is then introduced into the organ to the site and a biopsy is obtained. The cannula is typically integrated with the ultrasound transducer, and the cannula as well as the site in the image from which the cannula is poised to obtain a biopsy is indicated in the image. After obtaining the biopsy, another 2D image of another region of the organ or tissue may be obtained (by moving the ultrasound transducer) and an additional site of the organ or tissue may be selected for obtaining a biopsy. This process may be repeated several times so as to yield a number of biopsies from different sites of the organ or tissue.

In this method of obtaining biopsies, it is difficult for the practitioner to visualize in three dimensions the spatial relationship among the biopsy sites. This is due to the fact that each time the practitioner moves the ultrasound transducer to obtain a new image, the practitioner must remember how the transducer was moved in order to visualize in his mind the spatial relationship between the presently and previously imaged regions and the perspectives from which the regions were imaged. The inability to accurately determinate and record the spatial relationships among the imaged regions often results in biopsies not being obtained from sites where a biopsy should have been obtained.

SUMMARY OF THE INVENTION

The present invention provides a system and method for selecting and recording biopsy sites within a body organ.

More in particular the present invention provides a method for selecting and recording biopsy sites in a body organ comprising:

a) obtaining a three-dimensional volume of backscattered Ultrasound data grid of a three-dimensional region of the organ;
b) obtaining a two-dimensional matrix of Ultrasound data of a two-dimensional sub-region of said organ;
c) positioning the two-dimensional matrix of Ultrasound data in the three-dimensional volume of backscattered Ultrasound data grid obtained in step (a);
d) optionally selecting one or more sites in the two-dimensional matrix of Ultrasound data where a biopsy is to be obtained; preferably the selection being based on the analysis of the two-dimensional matrices or three dimensional matrix of ultrasound backscattered signal's data using a processor configured to give such an indication by using a set of characterization algorithms tuned to find possible abnormalities in the analyzed tissue;
e) indicating in the three-dimensional volume of backscattered Ultrasound data grid and/or in the two-dimensional matrix of Ultrasound data any sites at which biopsies were obtained; and
f) optionally repeating steps (b) to (e) as required.

In an embodiment of the present invention, the method comprises the steps of:

a) obtaining a three-dimensional volume of backscattered Ultrasound data grid of a three-dimensional region of the organ;
b) obtaining a first two-dimensional matrix of Ultrasound data of a first two-dimensional sub-region of the three-dimensional region;
c) determining the position of the first two-dimension matrix of Ultrasound data in the three-dimensional volume of backscattered Ultrasound data grid. This determination step may be done in many different ways, either computational or mechanical: 1) By using reference points inserted during the analysis into the volume grid and sub grid of the organ 2) By relying on existing anatomical or artificial features (e.g. a bone feature or artificially inserted clips present in the reflections' volume grid and sub-grid). 3) Based upon the information about the orientation of the transducer relative to the body organ when the volume grid and sub-grid were obtained. The sub-grid can then be indicated on the display within the volume grid representation of the organ.

The next step d) consists of optionally selecting one or more sites in the first two-dimensional matrix of Ultrasound data where a biopsy is to be obtained; optionally, said selection can be done directly in the three-dimensional volume of backscattered Ultrasound data grid, and the presentation of the selection for the medical practitioner can be on a two-dimensional gray scale view of a two-dimensional matrix of Ultrasound data.

Then e) indicating in the three-dimensional volume of backscattered Ultrasound data grid and/or in the two-dimensional matrix of Ultrasound data any sites at which biopsies were obtained; the indicating step can be accomplish in many ways. One way is to consider the "recommended" sites for biopsy, the selection being based on the analysis of the two-dimensional matrices or three dimensional matrix of ultrasound backscattered signal's data using a processor configured to give such an indication by using a set of characterization algorithms tuned to find possible abnormalities in the analyzed tissue. Another way is to calculate the correspondence/registration between the two-dimensional matrices comprising the three-dimensional volume of backscattered Ultrasound data grid and the scanned body organ, as described earlier. Thus, the exact position of the biopsy place can be determined in each two-dimensional Ultrasound data matrix by knowing the orientation of the probe with respect to the body organ and the length of the probe biopsy shut (further referred to as the cannula and shaft length).

f) obtaining an additional two-dimensional matrix of Ultrasound data of an additional two-dimensional sub-region of the organ, the additional two-dimensional sub-region being included in the three-dimensional region;
g) determining the position of the additional two-dimensional matrix of Ultrasound data in the three-dimensional volume of backscattered Ultrasound data grid;

h) indicating in the additional two-dimensional matrix of Ultrasound data any sites where biopsies have previously been obtained;
i) optionally selecting one or more sites in the additional two-dimensional matrix of Ultrasound data where additional biopsies are to be obtained; and
j) repeating steps f) to i) as required.

In an embodiment of the present invention, the three-dimensional volume of backscattered Ultrasound data grid of the organ is obtained by three-dimensional ultrasound. Said three-dimensional volume of backscattered Ultrasound data grid can then be displayed as a grid representation showing the three-dimensional contour of the organ. In another embodiment of the present invention, the three-dimensional volume of backscattered Ultrasound data grid of the organ is obtained by two-dimensional ultrasound. For example, by using 2D ultrasound systems regulated by an external motor. This will allow successive acquisition of successive two-dimensional matrices that will form eventually a three-dimensional volume Ultrasound data grid of the organ.

In an embodiment of the present invention, said one or more two-dimensional matrix of Ultrasound data can be obtained by two-dimensional and/or by three-dimensional Ultrasound.

Once the two-dimensional matrix of Ultrasound data is analyzed and its position further determined on the grid representation of the organ, a biopsy at a selected site may then be obtained. The two-dimensional matrix of Ultrasound data is analyzed by the processor which is configured to determine locations suspected of having a malignant behavior, as described hereunder.

The present method further encompassed the step of determining in the three-dimensional volume of backscattered Ultrasound data grid locations suspected of having a predetermined condition and indicating suspected locations in the displayed representation of the three-dimensional volume of backscattered Ultrasound data grid. Non-limiting examples of said predetermined condition can be a cyst, a polyp, a malignancy and the like. In a preferred embodiment, said predetermined condition is a malignancy. First, the 3D or 2D data grid locations, within a three-dimensional region of interest, suspected of having a predetermined condition are identified by the processor by means of characterization algorithms. Then, the position of the corresponding grid location are indicated in the two-dimensional matrices of Ultrasound data which then, as described hereinabove, are identified in the three-dimensional volume of backscattered Ultrasound data grid.

The present invention further provides a system for selecting and recording biopsy sites in a body organ comprising:
(a) A three-dimensional imaging device suitable for providing a three-dimensional volume Ultrasound data grid of a three-dimensional region of the organ and/or a two-dimensional matrix of Ultrasound data of a sub-region of said organ;
(b) One or more display screens suitable for displaying a representation of the three-dimensional volume of backscattered Ultrasound data grid and for displaying one or more two-dimensional views of two-dimensional matrix of Ultrasound data;
(c) Means for selecting one or more sites in a three-dimensional volume grid and/or in a two-dimensional view where a biopsy is to be obtained;
(d) A processor configured to:
  (a) determine the position of a region of interest in the three-dimensional volume of backscattered Ultrasound data grid;
  (a') analyze the region of interest for suitable biopsy site,
  (b) determine the position of a two-dimensional matrix of Ultrasound data in the three-dimensional volume grid;
  (c) display on a display screen a representation of a three-dimensional volume of backscattered Ultrasound data grid with an indication of the position of a two-dimensional frame in the three-dimensional volume grid;
  (d) display on a display screen one or more two-dimensional matrix of Ultrasound data;
  (e) determine in a three-dimensional volume of backscattered Ultrasound data grid any sites at which biopsies were obtained and indicate in a displayed representation of the three-dimensional volume of backscattered Ultrasound data grid any sites at which biopsies were obtained and/or any sites at which biopsies should have been obtained.

Suitable steps and methods for determining suitable or previous biopsy sites comprise the following: For already obtained biopsies: these biopsy sites are registered within the three-dimensional volume of backscattered Ultrasound data grid. If suitable biopsy sites are to be obtained: as described above, the practitioner marks a three-dimensional region of interest within the three-dimensional volume of backscattered Ultrasound data grid and then, the processor by means of applying the characterization algorithms to the data, will indicate the possible candidates from were biopsies are to be obtained. Again, these positions will be registered within the three-dimensional volume of backscattered Ultrasound data grid.

In an embodiment of the present invention, the present system comprises:
(a) A three-dimensional or a two dimensional imaging device providing a three-dimensional volume matrix of Ultrasound data of a three dimensional region of the organ;
(b) A two-dimensional or a three-dimensional imaging device providing two-dimensional matrix of Ultrasound data of two-dimensional sub-regions of the three-dimensional region;
(c) One or more display screens for displaying a representation of the three-dimensional volume matrix of Ultrasound data and for displaying one or more two-dimensional views of two-dimensional matrix of Ultrasound data;
(d) Means for selecting one or more sites in a three-dimensional volume grid and/or in a two-dimensional view where a biopsy is to be obtained;
(e) A processor configured to:
  (a) determine the position of a two-dimensional frame in the three-dimensional volume of backscattered Ultrasound data grid;
  (b) display on a display screen a grid representation of a three-dimensional volume matrix of backscattered Ultrasound data with an indication of the position of a two-dimensional frame in the three-dimensional volume;
  (c) display on a display screen one or more two-dimensional views of two-dimensional matrix of Ultrasound data,
  (c') analyze and locate in the three-dimensional volume of backscattered Ultrasound data, regions suspected of having a predetermined condition,
  (d) determine in a three-dimensional volume of backscattered Ultrasound data grid any sites at which biopsies were obtained and indicate in a displayed representation of the three-dimensional volume grid any sites at which biopsies were obtained; and/or any sites at which biopsies should have been obtained.

In an embodiment of the present invention, said system further comprises a device for obtaining a biopsy at a selected site.

According to the present invention, the processor can be further configured to determine in a three-dimensional volume of backscattered Ultrasound data grid, locations suspected of having a predetermined condition and indicating suspected locations in a displayed representation of the three-dimensional volume of backscattered Ultrasound data. In an embodiment the predetermined condition is a malignancy. The processor can be any commercially available CPU that is enabled by means of a commercially available operating system or a specially developed one to apply the characterization algorithms and other algorithms (e.g. correlation algorithms) on the three-dimensional volume of backscattered Ultrasound data. Following this application, specific mathematical features corresponding to the morphology of the underlying tissue are extracted. The characterization algorithms can be based on computing features like entropy, FFT parameters, wavelets parameters, correlation measures, and are tuned to quantify the probability of the analyzed tissue to be categorized as malignant or non-malignant tissue.

In an embodiment, the characterization algorithms are selected from the group comprising a Fourier analysis, a wavelet analysis and an entropy analysis. The characterization algorithms are calibrated to detect different tissue pathologies. The present inventors have identified the characteristic features that are related to a predetermined condition like healthy tissue, and those characteristic features that are related to a predetermined condition like malignant tissue. The meaning of "calibration" is the identification and selection of those features that are best separating the two pathological phenomena. This procedure is, of course, organ dependant.

Suitable characterization algorithms for performing the present invention are sufficiently sensitive to changes in the backscattered energy induced by the alterations in the tissue morphology typical of the disease to be detected. Suitable characterization algorithms are described in U.S. Pat. No. 6,785,570 and PCT application WO 2004/000125 the subject matter of which is incorporated herein by reference.

In an embodiment, a two-dimensional Fourier transform $$F(u, v) = \frac{1}{N} \sum_{u=0}^{N-1} \sum_{v=0}^{N-1} I(x, y) e^{-j\frac{2\pi}{N}(ux+vy)}$$

can be applied on a 20×20 pixel area (as also described further hereinbelow). The energy of each two-dimensional Fourier transform can then be measured by evaluating the sum of its Fourier coefficients.

In another embodiment, a two-dimensional discrete wavelet analysis on a pixel area (20×20 pixels) can be performed using the wavelet analysis software from the Matlab™ wavelet toolbox. A single-level two-dimensional wavelet decomposition using a particular wavelet type is performed. The output of this transformation consists of four matrices known as the principle image coefficients (A), horizontal coefficients (H), vertical image coefficients (V) and the diagonal coefficients (D). The contour graph of the coefficients of matrix A can be obtained, and the maximum of each contour graph can be used as an index. Other indices maybe also used in accordance with the invention when using wavelet analysis such as the maximum coefficient in sum of the coefficients matrices H, V and D. Other filters may be used in accordance with the invention such as a Mexican hat filter, as are known in the art. Then, a one-level one-dimensional wavelet analysis, using a particular wavelet type, is applied on the same pixel area.

In yet another embodiment, an entropy analysis may be performed on the analyzed 20×20 pixel area, wherein for each pixel I(x,y), a parameter A(x,y) can be calculated by $$A(x, y) = \frac{1}{n} \sum |I(x, y) - I(x', y')|^2$$

where the sum extends over all pixels (x',y') in a square neighborhood of the pixel situated at position (x,y), and n is the number of neighboring pixels (x',y') taken around the pixel (x,y). The entropy sum is then averaged by the number of neighboring pixels.

In an embodiment of the present invention, the three-dimensional imaging device is a three-dimensional ultrasound imaging device. Said three-dimensional volume of backscattered Ultrasound data can then be displayed as a grid representation showing the three-dimensional contour of the organ. The two-dimensional imaging device of the system according to the present invention can be a three-dimensional ultrasound imaging device.

The methods and systems described in this application can be applied to any organ to be examined, such as the prostate, the breast, the ovaries, the uterus, the vagina and the like. In a preferred embodiment, the organ is a prostate or breast.

The articles "a" and "an" are used herein to refer to one or to more than one, i.e. to at least one, the grammatical object of the article. By way of example, "a three-dimensional imaging device" means one three-dimensional imaging device or more than one three-dimensional device.

As used herein the term "three-dimensional volume of backscattered Ultrasound data grid" refers to a three-dimensional data matrix or image. Said term may be used interchangeably with "three-dimensional volume grid", "three-dimensional volume matrix of Ultrasound data", "volume grid", "three-dimensional volume of Ultrasound data", "3D image", "image", "3D matrix".

As used herein the term "two-dimensional matrix of Ultrasound data" refers to a two-dimensional image of a sub-region. Said term may be used interchangeably with "two-dimensional sub-image", "sub-image", "two-dimensional view", "planar image of a sub-region".

In accordance with the invention, a three-dimensional volume of backscattered Ultrasound data of at least a portion of the organ is obtained using a three-dimensional imaging device such as a three-dimensional ultrasound imaging transducer. The three-dimensional volume of backscattered Ultrasound data may be analyzed for regions that are suspected of having a predetermined condition such as a malignancy. For example, a selected three-dimensional region or the entire three-dimensional volume of backscattered Ultrasound data may be analyzed. The analysis is done for each two-dimensional matrix within the selected three-dimensional region or within the entire three-dimensional volume of backscattered Ultrasound data.

After the region of interest ("ROI") is defined, the characterization algorithms chosen for a specific predetermined condition (disease) are applied simultaneously on the volume data representing successive tissue slices within the ROI.

In an embodiment, the algorithms are applied successively to units of 20×20 consecutive pixels of data in the volume matrix. The size of 20×20 is not fixed and it may differ from organ to organ and all different unit sizes are encompassed herein. Furthermore, the shape of the unit is not limited to a square but can also be rectangular, or it may have different other shapes including but not limited to circle, ellipse and the like. The results of the algorithms are calculated independent from each other. In general, a 20×20 pixels unit maps onto a four sided area of approximately 2×2 mm of tissue size. The analysis procedure for each 20×20 pixel unit is composed of three successive groups of mathematical manipulations:

Each characterization algorithm generates a specific transformed matrix out of the 20×20 pixel units present in the original matrix.

From each transformed matrix, statistical features that discriminate between the "normal" and "abnormal" characteristics of the tissues are extracted.

For each algorithm a pre-defined threshold value is applied below which presence of cancer is not likely.

Each 20×20 pixels unit has its own characteristics (according to the different algorithms that are applied), independently from neighboring units.

When all 20×20 pixel units within the ROI have been analyzed by the characterization algorithms, an inspection of the results for the given ROI is performed. The purpose of this inspection is to indicate whether in a given ROI, there is indication of a predetermined condition (such as malignancy).

For example, applicant's co-pending U.S. patent application Ser. No. 09/874,919 filed on Jun. 5, 2001 discloses a method for detecting malignancies in a tissue. The three-dimensional image is processed to produce a grid-like three-dimensional representation of the three-dimensional contour of the organ herein referred as a "volume grid representation". This grid representation of the image is displayed on a display screen. The grid representation of the contour allows the interior of the organ to be visualized through the surface. Regions in the volume grid suspected of having a predetermined condition such as malignancy may be indicated in the grid representation. A sub-region of the organ is then imaged. The sub-region may be imaged using either a two-dimensional imaging system such as an ultrasound system having a two-dimensional transducer, or a three-dimensional imaging system. In a preferred embodiment the sub-region is imaged using a three-dimensional ultrasound transducer. The image of the sub-region, referred to herein as a "two-dimensional view" or "sub-image" or "two-dimensional matrix of Ultrasound data" is displayed on a display screen. The two-dimensional view is analyzed and its position within the grid representation of the organ is determined. This may be done by using one or more reference points that are present in the volume grid of the organ and the sub-image (e.g. a bone feature or artificially inserted clips present in the volume grid and sub-image). Alternatively, this may be done in a calculation based upon the orientation of the transducers relative to the body organ when the volume grid and sub-image were obtained. The sub-image is then indicated in the displayed grid representation of the organ. The sub-image and the grid representation showing the sub-image are thus displayed simultaneously. Regions in the sub-image or in the volume grid suspected of having the predetermined condition are preferably indicated in the displayed sub-image and/or in the volume grid.

The practitioner decides based on the processor analysis at which sites, if any, in the sub-image or in the volume grid, a biopsy is to be obtained. The locations of any biopsies obtained are indicated in the sub-image as well as in the grid-representation.

Additional two-dimensional views of the organ may then be obtained and displayed. For each sub-image, the position of the sub-image is indicated in the grid representation. Sites in the sub-image where biopsies were previously obtained are indicated in the sub-image. Sites in the sub-image suspected of having the predetermined condition are preferably indicated in the sub-image. The practitioner then decides at which sites, if any, in this sub-image, a biopsy is to be obtained. The locations of any biopsies obtained are indicated in the sub-image as well as in the grid-representation.

Since the location of a current-sub-image is indicated in the grid representation together with the locations of any previous sub-regions, the practitioner can select sub-images in an orderly fashion. If sites suspected of having a predetermined condition are indicated in the grid representation and in the sub-images, the practitioner can obtain biopsies from all suspected sites.

In a preferred embodiment, the transducer used to obtain sub-images has an integrated cannula that is used to obtain a biopsy at a site in a sub-image. The sub-image includes a sign indicative of the site in the sub-image from which the cannula is poised to remove tissue for a biopsy. This allows the practitioner to select a site from which a biopsy is to be obtained based upon the spatial relationship of the site to sites in the volume grid where biopsies were previously obtained. In particular, if suspected sites are indicated in the sub-image, the practitioner can position the cannula to obtain biopsies from the suspected sites.

The present invention permits to give prior to biopsy an indication for the region of interest in an organ imaged as a 3D volume of backscattered Ultrasound data grid using the present system and further allows the practitioner to pick up and/or mark the designated areas for biopsies. The systems and methods according to the invention permit to visually guide the practitioner to the right place in real time and permit to record the area(s) that where biopsies were taken for further follow-up and planning of treatment. The present invention allows to detect biopsies traces or sites by performing additional 3D imaging of the organ after the biopsy was taken.

DETAILED DESCRIPTION OF PREFERRED EMBODIMENTS

First Embodiment

Figure 1:
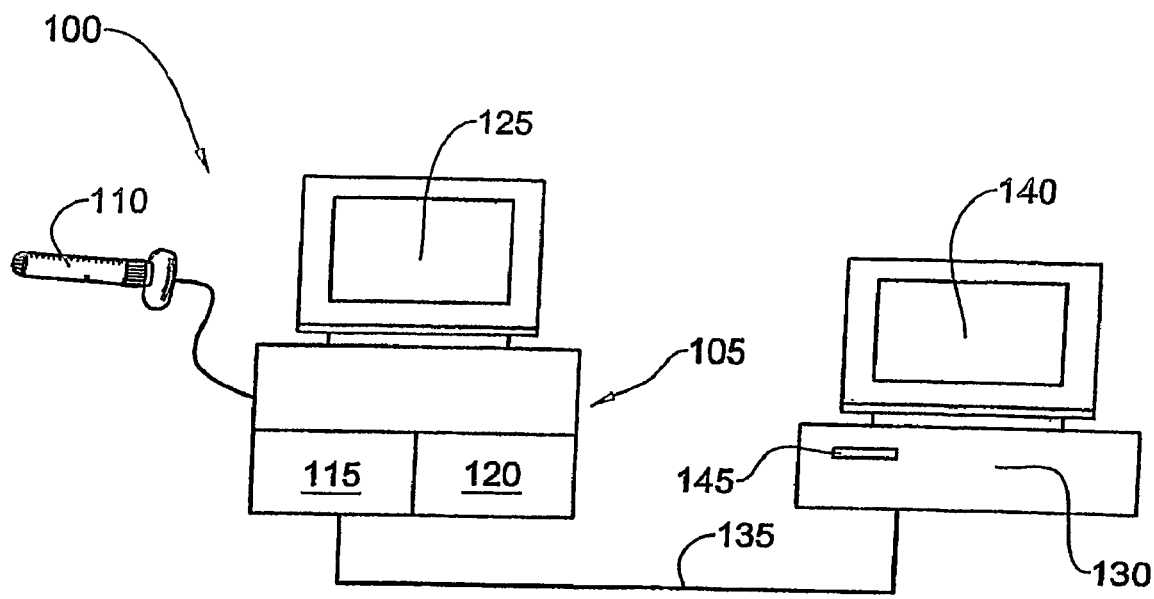
FIG. 1 shows a system, generally indicated by 100, for selecting and recording biopsy sites in an organ in accordance with one embodiment of the invention.

FIG. 1 shows a system, generally indicated by 100, for selecting and recording biopsy sites in an organ in accordance with one embodiment of the invention. The system 100 comprises a three-dimensional imaging device 105 that is used to obtain a three-dimensional volume grid of at least a portion of a body organ. The 3D imaging device 105 shown in FIG. 1 is a 3D ultrasound imaging device. This is by way of example only, and any 3D imaging device may be used in accordance with the invention. The imaging device 105 includes a transducer 110 that is positioned in the vicinity of the organ to be imaged to obtain a 3D volume grid of the organ. Said transducer 110 provides 3D data. The transducer 110 shown in FIG. 1 is adapted to be inserted into a rectum in order to image a prostate gland. This is also by way of example only. Said transducer 110 may have any suitable shape to be applied to the imaging of any organ such as the prostate, the breast, the ovaries, the uterus, the vagina and the like. An image captured by the transducer 110 is input to a processor 115 associated with the imaging device 105. The processor 115 is configured to store a captured image in a memory 120. The processor 115 is further configured to display a planar section of a captured image on a display screen 125.

Figure 2:
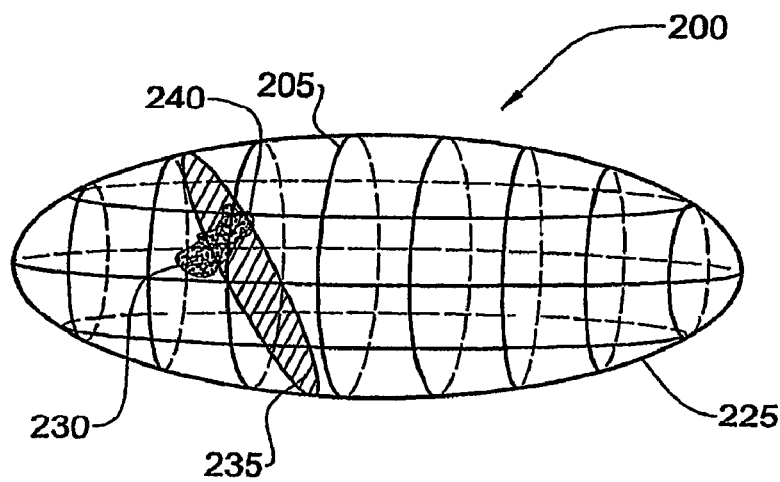
FIG. 2 shows a grid representation 200 of the surface of an organ.

A processor 130 is configured to analyze and process a captured 3D image. The processor 130 may be the same processor as the processor 115, or may be a separate processor, as shown in FIG. 1. In the latter case, data indicative of an image may be transmitted from the processor 115 to the processor 130 over a data transmission line 135. Alternatively, the data may be recorded on a data storage medium, such as a floppy disk, and manually inserted into a disk drive 140 associated with the processor 130. The processor 130 is configured to process a captured 3D image and to generate a 3D grid representation of the surface of the organ. FIG. 2 shows a grid representation 200 of the surface of an organ. In the grid representation 200, a discrete set of curves 205 are visualized on the surface of the organ, allowing the interior of the organ to be viewed.

Referring again to FIG. 1, the processor 130 is configured to display the grid representation on a display screen 140 which may be the display screen 125, or may be a different display screen. The processor 130 is preferably further configured to analyze a captured 3D image, and to detect regions of interest in the imaged organ suspected of having a predetermined condition, such as a malignancy. Suspected regions may be indicated in the displayed grid representation 200, by coloring the corresponding regions in the grid representation with a color that is different from the color of the curves 225. For example, the 3D region 230 in the grid representation 200 may be a region suspected of having the predetermined condition. The region 230 appears behind portions of the curves 225 in the foreground (represented by solid lines) and in front of portions of the curves 225 in the background (represented by broken lines).

Figure 3:
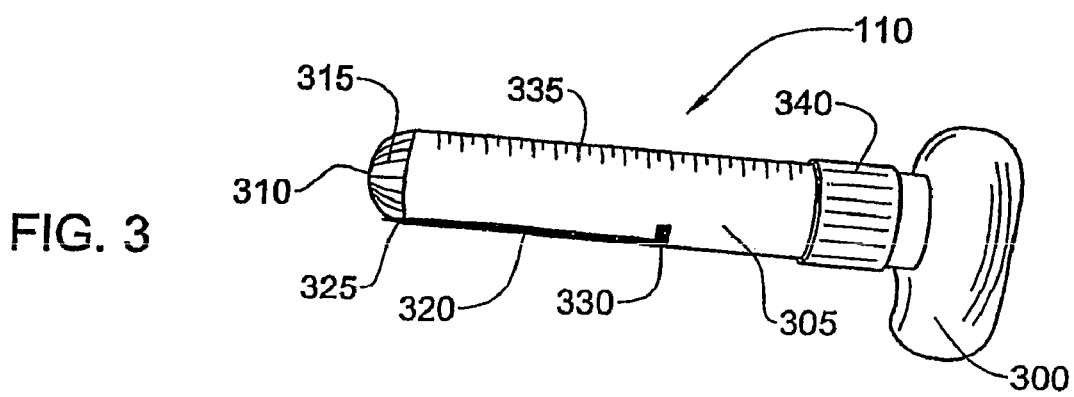
FIG. 3 shows the transducer 110 in greater detail.

FIG. 3 shows the transducer 110 in greater detail. The transducer 110 has a handle 300, and a shaft 305. The tip 310 of the shaft houses an array 315 of ultrasound transceivers that emit ultrasound waves and detect waves reflected from the body of a subject. The shaft 305 is dimensioned to be inserted though the subjects anus into the rectum. The transducer 110 also includes a cannula 320 that is used for obtaining biopsies. The cannula 320 has a trocar 325 at its tip for collecting biopsy material. The cannula 320 is slidable parallel to the shaft 305 by means of a handle 330, between a first position in which it does not extend beyond the tip, as shown in FIG. 3, and a second position in which it extends beyond the tip 315 (not shown), for collecting biopsy material. The shaft 305 is inserted into the body with the cannula 320 not extending beyond the tip of the shaft. When biopsy material is to be collected, as described below, the cannula 320 is translated along the shaft 305 so that the cannula 320 extends beyond the tip, until the trocar 325 has arrived at the site where biopsy material is to be collected.

The shaft 305 contains a set of calibration marks 335 along its length that allow determination of the depth of insertion of the shaft 305 into the body. The transducer also includes a linear and angular acceleration detector 340 that surrounds the shaft 305. The linear and angular acceleration detector 340 allows determination of the change in the translational and angular position of the transceiver array 315 in space when the transceiver array 315 is moved from a first position to a second position. Changes in the spatial orientation of the shaft 305 as determined from the detector 340 are input to the processor 130. The processor 130 is configured to determine from the inputted readings the current location and spatial orientation of the transceiver array 315 in the body relative to a previous location and spactial orientation of the transceiver array 315.

After a 3D image of the organ has been obtained and a grid representation of the organ generated and displayed, as described above, a 2D sub-image or view of a planar sub-region of the organ is obtained using the imaging device 105. The 2D sub-region is displayed on the display screen 140 next to the grid representation 200 of the organ. The location and spatial orientation of the transceiver array 315 when the sub-image is obtained may or may not be the same as that when the 3D image was obtained. However, any change in the spatial orientation of the transceiver array 315 that occurred when the transceiver array 315 was moved from its position when the 3D image was obtained to its position when the 2D sub-image was obtained is known from the angular acceleration detector 340. Therefore, the location of the sub-image within the 3D volume grid can be determined. The processor 130 is configured to indicate this sub-region in the grid representation 200, preferably using a different color from the color used to indicate the grid lines 225 and suspected regions, such as the suspected region 230. FIG. 2 shows representation of an imaged planar sub-region 235 in the grid representation 200. The planar sub-region 235 intersects the suspected region 230. The intersection of the planar sub-region 235 with suspected regions, such as the suspected region 230, is indicated in the image of the sub-region 235 on the display screen.

The processor 130 is further configured to indicate in the displayed image of the sub-region the site where the cannula 320 is poised to obtain biopsy material. For example, the dot 240 in FIG. 2 shows that the cannula is poised to obtain a biopsy from the vicinity of the dot 240 in the sub-region 235. The practitioner thus manipulates the transducer 110 so as to position the transceiver array 315 into a location and spatial orientation producing a sub-image in which the cannula 320 is poised to obtain biopsy material from a site which the practitioner has selected. Biopsy material is then obtained from the selected site. The site in the organ from which biopsy material was obtained is indicated in the grid representation 200.

Additional 2D sub-images of the organ may then be obtained, as processed as above. For each sub-image, the position of the sub-image in the 3D volume grid is indicated in the grid-representation of the organ. Locations in the sub-image suspected of having the predetermined condition, as well as sites in the sub-image where biopsies were previously performed, are indicated in the displayed volume grid. The site in the sub-image at which the cannula 320 is poised to obtain biopsy material is also indicated in the three-dimensional volume grid. If the practitioner decides to obtain biopsy material from this site, a biopsy is obtained.

Indicating in the grid-representation the site in the organ of each biopsy as the biopsy is obtained insures that biopsies are obtained from all selected sites, and moreover allows the site of each biopsy in the organ to be recorded for future reference. Displaying simultaneously on a displayed sub-image regions suspected of having a predetermined condition, such as malignancy as well as the site where the cannula 320 is poised to obtain biopsy material, allows biopsies to be made in the suspected regions.

Second Embodiment

Figure 4:
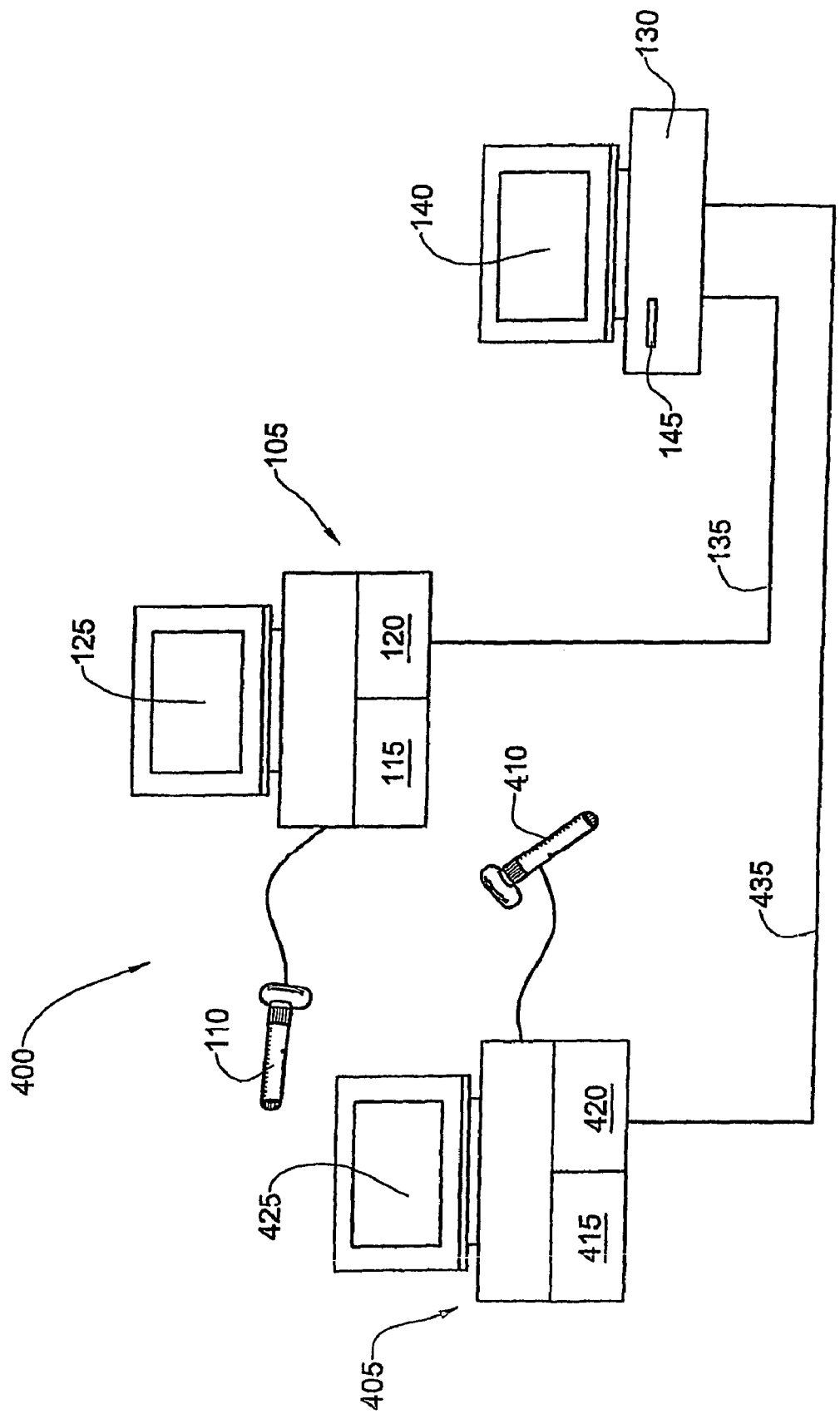
FIG. 4 shows a system, generally indicated by 400, for selecting and recording biopsy sites in an organ in accordance with another embodiment of the invention.

FIG. 4 shows a system, generally indicated by 400, for selecting and recording biopsy sites in an organ in accordance with another embodiment of the invention. The system 400 has components in common with the system 100, and similar components in the two systems are identified by the same reference numeral, without further explanation. In contrast to the system 100 in which the imaging device 105 is used to obtain a 3D image of a body organ as well as 2D sub-images, the system 400 comprises a three-dimensional imaging device 105 that is used to obtain only three-dimensional images of at least a portion of a body organ. A separate imaging device 405 is used to obtain two-dimensional sub-images of the organ. The imaging device 405 will be referred to herein as a "2D imaging device", although it may in fact be capable of 3D imaging. The 2D imaging device 405 shown in FIG. 4 is a 2D ultrasound imaging device. This is by way of example only, and any 2D imaging device may be used in accordance with the invention. The imaging device 405 includes a transducer 410 that is positioned in the vicinity of the organ to be imaged to obtain a 2D sub-image of the organ. The transducer 410 shown in FIG. 4 is adapted to be inserted into a rectum in order to image a prostate gland. This is also by way of example only. A sub-image captured by the transducer 410 is input to a processor 415 associated with the imaging device 405. The processor 415 is configured to store a captured sub-image in a memory 420. The processor 415 is further configured to display a sub-image on a display screen 425.

The processor 130 is configured to analyze and process a captured 2D sub-image. The processor 130 may be the same processor as the processor 115 or the processor 415, or may be a separate processor, as shown in FIG. 4. In the latter case, data indicative of an image may be transmitted from the processor 415 to the processor 130 over a data transmission line 435. Alternatively, the data indicative of a sub-image may be recorded on a data storage medium, such as a floppy disk, and manually inserted into the disk drive 140 associated with the processor 130.

Since separate imaging devices are used to obtain the 3D image and 2D sub-images, the 3D image obtained by the imaging device 105 must contain one or more identifiable reference points that may be for example, a bone feature or clips artificially introduced into the organ. The processor 130 is configured to process a captured 3D image obtained by the 3D imaging system 105 and to generate a 3D volume grid representation of the surface of the organ, as was explained in The first embodiment in reference to FIG. 2. The processor 130 is configured to display the grid representation on a display screen 140 which may be the display screen 125, the display screen 425, or may be a different display screen, as shown in FIG. 4. The processor 130 is preferably further configured to analyze a captured 3D image, and to detect regions in the imaged organ suspected of having a predetermined condition, such as a malignancy. Suspected regions may be indicated in the displayed grid representation 200, by coloring the corresponding regions in the grid representation with a color that is different from the color of the curves 225, as described in The first embodiment.

Figure 5:
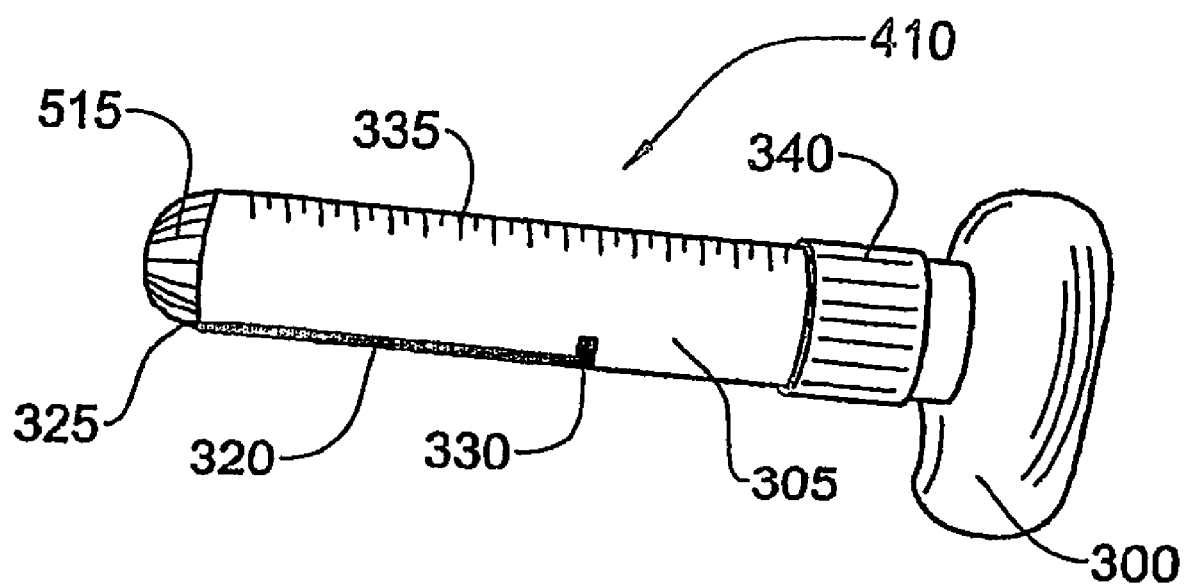
FIG. 5 shows the transducer 410 in greater detail.

FIG. 5 shows the transducer 410 in greater detail. The transducer 410 is in principle similar in shape and structure to the transducer 110, since both transducers are used to image the same organ. The transducer has several components in common with the transducer 110, and similar components are indicated by the same reference numeral without further explanation. In particular, the shaft 305 of the transducer 410 contains a set of calibration marks 335 along its length and a linear and angular acceleration detector 340 that surrounds the shaft 305. The tip 310 of the shaft 305 houses an array 515 of ultrasound transceivers that emit ultrasound waves and detect waves reflected from the body of a subject. The depth of penetration of the shaft 305 in the body as determined from the calibration marks 335 or from inserted clips.

The transducer 410 also includes a cannula 320 that is used for obtaining biopsies, as described in Example 1. Unlike the transducer 110 of the system 100, the transducer 110 of the system 400 need not have a cannula, as only the transducer 410, and not the transducer 110, is used for obtaining biopsies with the system 400.

After a 3D image of the organ has been obtained by the 3D imaging device 105, and a volume grid representation of the organ generated and displayed, as described above, a 2D sub-image of a planar sub-region of the organ is obtained using the imaging device 405. The 2D sub-image must contain the reference points present in the 3D image in order to determine the difference between the position and spatial orientation of the transceiver array 315 when the 3D image was obtained, and the transceiver array 515 when the 2D sub-image was obtained. The position of the transceiver array 515 when the 2D sub-image was obtained is preferably the same as that of the transceiver array 315 when the 3D image was obtained. The location of the sub-image obtained by the 2D imaging device 405 in the 3D image obtained by the 3D imaging device 105 can therefore be determined. The 2D sub-region is displayed on the display screen 140 next to the grid representation 200 of the organ. The processor 130 is configured to indicate this sub-region in the grid representation 200, as described in the first embodiment in reference to FIG. 2.

The processor 130 is further configured to indicate in the displayed image of the sub-region the site where the cannula 320 on the transducer 410 is poised to obtain biopsy material, as explained in The first embodiment. The practitioner thus manipulates the transducer 410 so as to position the transceiver array 515 into a location and spatial orientation producing a sub-image in which the cannula 320 of the transducer 410 is poised to obtain biopsy material from a site which the practitioner has selected. Biopsy material is then obtained from the selected site. The site in the organ from which biopsy material was obtained is indicated in the grid representation 200.

As in The first embodiment, additional 2D sub-images of the organ may then be obtained, as described above. For each additional 2D sub-image, the change in the location and angular orientation of the transducer 410 that occurred when it was moved after the previous 2D sub-image was obtained, is determined from the linear and angular acceleration detector 340 on the transducer 410. For each sub-image, the position of the sub-image in the 3D volume grid is indicated in the grid-representation of the organ. Locations in the sub-image suspected of having the predetermined condition, as well as sites in the sub-image where biopsies were previously performed, are indicated in the displayed image. The site in the sub-image at which the cannula 320 of the transducer 410 is poised to obtain biopsy material is also indicated in the image. If the practitioner decides to obtain biopsy material from this site, a biopsy is obtained.

Indicating in the grid-representation the site in the organ of each biopsy as the biopsy is obtained insures that biopsies are obtained from all selected sites, and moreover allows the site of each biopsy in the organ to be recorded for future reference. Displaying simultaneously on a displayed sub-image regions suspected of having a predetermined condition, such as malignancy as well as the site where the cannula 320 of the transducer 410 is poised to obtain biopsy material, allows biopsies to be made in the suspected regions.

What is claimed is:

1. A method for selecting and recording biopsy sites in a body organ in real time comprising:
   a) obtaining a three-dimensional volume of data from a 3-dimensional imaging device producing backscattered ultrasound data of a three-dimensional region of the organ;
   b) obtaining a two-dimensional matrix of ultrasound data from a 2-dimensional imaging device producing additional ultrasound data of a two-dimensional sub-region of said organ, which is the same or different from the device of step a);
   c) positioning the two-dimensional matrix of ultrasound data in the three-dimensional volume of backscattered ultrasound data obtained in step (a);
   d) applying a characterization algorithm to the 3-dimensional volume of data and selecting a region in the 3-dimensional volume of data suspected of having a predetermined condition using a processor configured to determine presence of said condition;
   e) producing and displaying a 3-dimensional image from the 3-dimensional data and 2-dimensional matrix, and indicating on said image the identified region suspected of having a predetermined condition;
   f) indicating in the displayed image a position within the 2-dimensional matrix of a device poised to obtain biopsy material from a site in the organ;
   g) obtaining biopsy material from the device; and
   h) indicating in the displayed 3-dimensional image the site in the organ from which the biopsy material was obtained.

2. The method according to claim 1, wherein steps (b) to (f) comprise
   b1) obtaining a first two-dimensional matrix of ultrasound data of a first two-dimensional sub-region of the three-dimensional region;
   c1) determining the position of the first two-dimensional matrix of ultrasound data in the three-dimensional volume of ultrasound data obtained in step (a);
   d1) indicating in the three-dimensional volume of ultrasound data and/or in the two-dimensional matrix of ultrasound data any sites at which biopsies were obtained;
   e1) obtaining an additional two-dimensional matrix of ultrasound data of an additional two-dimensional sub-region of the organ, the additional two-dimensional sub-region being included in the three-dimensional region;
   f1) determining the position of the additional two-dimensional matrix of ultrasound data in the three-dimensional volume of ultrasound data;
   f2) indicating in the additional two-dimensional matrix of ultrasound data any sites where biopsies have previously been obtained;
   h1) repeating steps e1) to f2) at least once.

3. The method of claim 2, further comprising selecting one or more sites in the first two-dimensional matrix of ultrasound data where a biopsy is to be obtained after step c1.

4. The method of claim 2, further comprising selecting one or more sites in the additional two-dimensional matrix of ultrasound data where additional biopsies are to be obtained after step f2.

5. The method according to claim 1, wherein step (a) is performed on an organ selected from prostate or breast.

6. The method according to claim 1, wherein the two-dimensional matrix of ultrasound data of step (b) is obtained using the three-dimensional ultrasound imaging device of step (a).

7. The method according to claim 1, wherein the predetermined condition is a malignancy.

8. The method of claim 1, further comprising the step of selecting one or more sites in the two-dimensional matrix of ultrasound data where a biopsy is to be obtained after step c.

9. The method of claim 1, further comprising repeating steps b) to h) at least once.

10. A system for selecting and recording biopsy sites in a body organ comprising:
    (a) a three-dimensional imaging device configured for providing a three-dimensional volume of backscattered ultrasound data of a three-dimensional region of the organ and/or a two-dimensional matrix of ultrasound data of a sub-region of said organ;
    (b) one or more display screens configured for displaying in real time a representation of the three-dimensional volume of backscattered ultrasound data and for displaying one or more two-dimensional views of said two-dimensional matrix of ultrasound data;
    (c) means for selecting in real time one or more sites in said three-dimensional volume and/or in said two-dimensional view where a biopsy is to be obtained; and
    (d) a processor configured to:
       determine in real time the position of a region of interest in the three-dimensional volume of backscattered ultrasound data;
       (ii) determine in real time the position of said two-dimensional matrix of backscattered ultrasound data in the three-dimensional volume;
       (iii) display on a display screen in real time a representation of a three-dimensional volume of backscattered ultrasound data with an indication of the position of one or more two-dimensional views in the three-dimensional volume;
       (iv) display on a display screen one or more two-dimensional matrices of ultrasound data; and
       (v) determine in said three-dimensional volume of backscattered ultrasound data locations suspected of having a predetermined condition and indicating suspected locations in said displayed representation of the three-dimensional volume of ultrasound data,
       (vi) determine in said three-dimensional volume of backscattered ultrasound data any sites at which biopsies were obtained and indicate in said displayed representation of the three-dimensional volume of backscattered ultrasound data any sites at which biopsies were obtained and/or any sites at which biopsies should have been obtained.

11. The system according to claim 10, further comprising a cannula for obtaining a biopsy at a selected site.

12. The system according to claim 10 wherein the predetermined condition is a malignancy.

13. A system comprising:
    (a) a three-dimensional imaging device configured for providing a three-dimensional volume of backscattered ultrasound data of a three-dimensional region of the organ;

a1) a two-dimensional or a three-dimensional imaging device configured for providing two-dimensional matrix of ultrasound data of two-dimensional sub-regions of the three-dimensional region;
(b) one or more display screens configured for displaying in real time a representation of the three-dimensional volume of backscattered ultrasound data and for displaying one or more two-dimensional views of said two-dimensional matrix of ultrasound data;
(c) means for selecting in real time one or more sites in said three-dimensional volume and/or in said two-dimensional view where a biopsy is to be obtained; and
(d) a processor configured to:
  i) determine the position of a two-dimensional frame in the three-dimensional volume of ultrasound data;
  ii) display on a display screen a grid representation of a three-dimensional volume matrix of ultrasound data with an indication of the position of said two-dimensional frame in the three-dimensional volume;
  iii) display on a display screen one or more two-dimensional views of said two-dimensional frame of ultrasound data; and
  iv) determine in said three-dimensional volume of ultrasound data any sites at which biopsies were obtained and indicate in a displayed representation of the three-dimensional volume any sites at which biopsies were obtained and/or any sites at which biopsies should have been obtained.

\* \* \* \* \*

UNITED STATES PATENT AND TRADEMARK OFFICE
CERTIFICATE OF CORRECTION

PATENT NO. : 7,824,339 B2
APPLICATION NO. : 11/251435
DATED : November 2, 2010
INVENTOR(S) : Dror Nir It is certified that error appears in the above-identified patent and that said Letters Patent is hereby corrected as shown below:

Column 2, Line 19, "two-dimension matrix" should be changed to --two-dimensional matrix--

Column 10, Line 8, "location and spactial" should be changed to --location and spatial--

Column 14, Line 34, Claim 10 "determine in real time" should be changed to --(i) determine in real time--

Signed and Sealed this
Twelfth Day of April, 2011

David J. Kappos
*Director of the United States Patent and Trademark Office*